United States Patent [19]

Adachi et al.

[11] Patent Number: 5,250,686
[45] Date of Patent: Oct. 5, 1993

[54] PROCESS FOR PRODUCING TRIAZINE COMPOUNDS

[75] Inventors: Ryoichi Adachi; Kazufumi Nakamura; Masahiro Nishii; Masahiro Yoshida; Izumi Terada; Hidetoshi Koga, all of Sodegaura, Japan

[73] Assignee: Idemitsu Kosan Company Limited, Tokyo, Japan

[21] Appl. No.: 868,727

[22] Filed: Apr. 14, 1992

[30] Foreign Application Priority Data

Apr. 18, 1991 [JP] Japan ................................ 3-087000

[51] Int. Cl.⁵ ........................................ C07D 251/18
[52] U.S. Cl. .................................................. 544/206
[58] Field of Search ......................................... 544/206

[56] References Cited

U.S. PATENT DOCUMENTS

| 2,926,165 | 2/1960 | Shapiro et al. | 260/249.9 |
| 3,767,656 | 10/1973 | Diamond et al. | 260/249.9 |
| 3,816,419 | 6/1974 | Cross et al. | 260/249.9 |

FOREIGN PATENT DOCUMENTS 0411153 2/1991 European Pat. Off.
WO90/09378 8/1990 Japan.

OTHER PUBLICATIONS

Purrington et al., "Preparation of α-Fluoro Carboxylic Acids and Derivatives", J. Org. Chem., 1990, 55, 3423-3424.
Gensler et al., "Fluorination of Methyl Isobutyrate with Perchloryl Fluoride", J. Org. Chem., vol. 33, No. 11, 1968, Notes 4279-4281.
E. M. Smolin et al., "s-Triazines and Derivatives", (The Chemistry of Heterocyclic Compounds), Jun. 1967, pp. 226-229, Interscience Publishers Inc., New York US.

*Primary Examiner*—John M. Ford
*Attorney, Agent, or Firm*—Frishauf, Holtz, Goodman & Woodward

[57] ABSTRACT

A process for producing a triazine derivative of the formula (III),

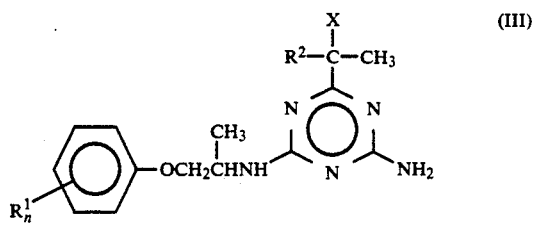

wherein $R^1$ is a $C_1$-$C_4$ alkyl group, n is an integer of 0 to 2, $R^2$ is hydrogen or a $C_1$-$C_2$ alkyl group, and X is a halogen atom, which comprises reacting a biguanide derivative of the formula,

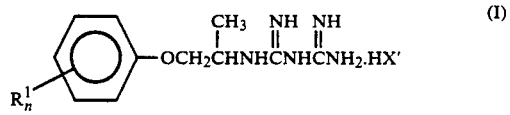

wherein $R^1$ and n are as defined in the formula (III), and X' is a halogen atom, with a halocarboxylic acid ester of the formula,

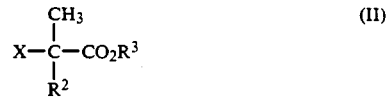

wherein $R^2$ and X are as defined in the formula (III), and $R^3$ is a $C_1$-$C_4$ alkyl group, in the presence of a base, wherein a dehydrating agent is present in the reaction system, and processes for producing 2-fluoroisobutyric acid ester as an intermediate compound for the production of the triazine derivative.

20 Claims, No Drawings

PROCESS FOR PRODUCING TRIAZINE COMPOUNDS

BACKGROUND OF THE INVENTION

1. Field of the Invention

The present invention relates to a process for producing a triazine derivative useful as a herbicide and a process for producing an intermediate compound for the production of the triazine derivative.

2. Description of the Prior Arts

As a triazine-type herbicide, WO90/09378 discloses a triazine derivative in which a phenoxyalkylamino group is substituted on a triazine ring, as is shown in the following formula. This publication describes that the above triazine derivative has remarkable advantages that it not only has excellent herbicidal effect but also exhibits no phytotoxicity on paddy rice.

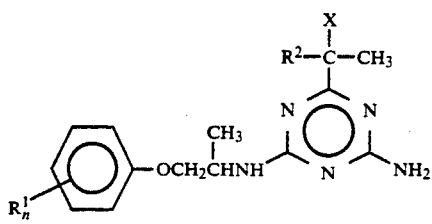

wherein $R^1$ is a $C_1$-$C_4$ alkyl group, n is an integer of 0 to 2, $R^2$ is hydrogen or $C_1$-$C_2$ alkyl group, and X is a halogen atom.

The above publication discloses a process for producing the above triazine derivative, which comprises reacting a biguanide derivative such as 2-phenoxy-1-methylethyl biguanide with a halocarboxylic acid ester such as 2-fluoroisobutyric acid ester in the presence of a base. This process is specifically illustrated by the following reaction scheme.

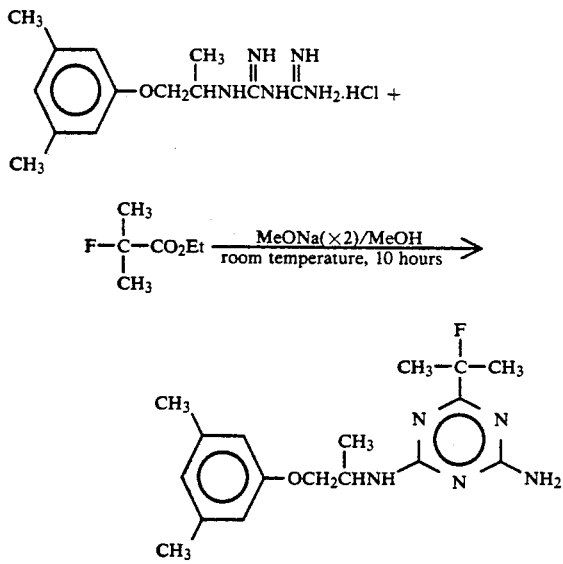

However, the process for producing a triazine derivative, described in the above WO90/09378, has the following defect; The halocarboxylic acid ester as one of the starting materials is hydrolyzed due to water formed as a byproduct in the reaction, and the reaction between the biguanide derivative and the halocarboxylic acid ester therefore cannot be quantitatively carried out. Hence, the yield of the intended triazine derivative is low. This defect can be overcome to some extent by using an excess amount of the halocarboxylic acid ester relative to the biguanide derivative as a starting material. In this case, however, the amount of the halocarboxylic acid ester increases, and the production cost consequently increases.

Meanwhile, 2-fluoroisobutyric acid ester, one of halocarboxylic acids used for the production of the above triazine derivative, is obtained, for example, by carrying out a halogen exchange reaction in which AgF is allowed to act on 2-bromoisobutyric acid ester for halogen exchange in the absence of a solvent (J. Org. Chem. 33 4279 (1968)). This process is illustrated by the following reaction scheme.

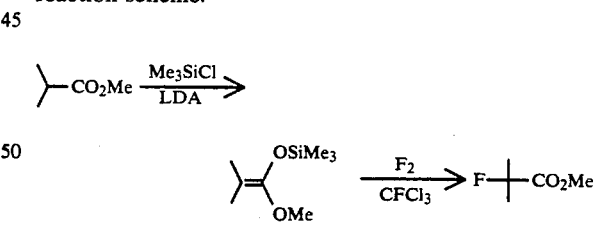

In the above conventional process, methacrylic acid ester is formed as a byproduct at a step of producing 2-fluoroisobutyric acid ester from 2-bromoisobutyric acid ester. Therefore, the defect with this process is that the selectivity to the intended substance, 2-fluoroisobutyric acid ester, is as low as 20%. Further, there are also another defect in that AgF as a reagent for the halogen exchange reaction is expensive and the production cost inevitably increases.

Further, J. Org. Chem. 55 3423 (1990) discloses a process for producing 2-fluoroisobutyric acid ester, in which trimethylsilyl chloride is allowed to react with methyl isobutyrate in the presence of lithium diisopropylamine (LDA) to prepare 1-methoxy-1-(trimethylsilyloxy)-2-methylpropene, and then $F_2$ is allowed to react therewith in $CFCl_3$ to obtain 2-fluoroisobutyric acid ester. This process is illustrated by the following reaction scheme.

The defect with the above conventional process using methyl isobutyrate as a raw material is that it uses a two-step reaction and the yield of the intended product decreases. There is also another defect that the reactions in the first and second steps are required to be carried out at an extremely low temperature of $-78°$ C. and therefore special equipment such as a refrigerator is required.

Further, as shown in the following reaction schemes, there are also an HF addition reaction of methacrylic acid ester and a substitution reaction using HF in which a hydroxy group of hydroxyisobutyric acid ester is replaced with fluorine.

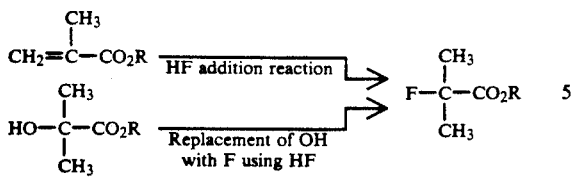

In the above processes, however, HF is a highly toxic reagent and difficult to handle, and further, the reactions frequently entail a side reaction. It is therefore difficult to control these reactions.

SUMMARY OF THE INVENTION

It is a first object of the present invention to provide a process for producing a triazine derivative useful as a herbicide at high yields and at a low cost.

Further, it is a second object of the present invention to provide a process for producing 2-fluroisobutryic acid ester, one of intermediate compounds for the production of the triazine derivative, from methacrylic acid ester as a starting material at a single reaction step by means of simple equipment, with high selectivity and at a low cost.

Furthermore, it is a third object of the present invention to provide a process for producing 2-fluoroisobutyric acid ester at high yields, safely and at a low cost without using highly toxic HF and without using any expensive reagent such as AgF.

According to the present invention, the above first object of the present invention is achieved by a process for producing a triazine derivative (III) to be specified below, which comprises reacting a biguanide derivative (I) to be specified below with a halocarboxylic acid ester (II) to be specified below in the presence of a base, wherein a dehydration agent is present in the reaction system.

The above second object of the present invention is achieved by a process for producing 2-fluoroisobutyric acid ester, which comprises reacting a hydrogen fluoride source with a methacrylic acid ester (IV) to be specified below.

The above third object of the present invention is achieved by a process for producing 2-fluoroisobutyric acid ester of the formula (VII) to be specified below, which comprises reacting a haloisobutyric acid ester (VI) to be specified below with a metal fluoride in the presence of a solvent.

Therefore, the gist of the first aspect of the present invention consists in a process for producing a triazine derivative of the formula (III),

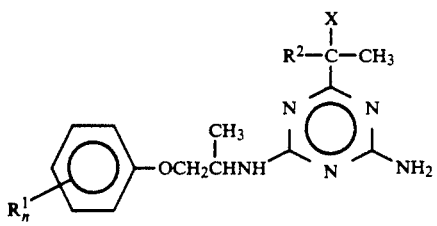

wherein $R^1$ is a $C_1$-$C_4$ alkyl group, n is an integer of 0 to 2, $R^2$ is hydrogen or a $C_1$-$C_2$ alkyl group, and X is a halogen atom,
which comprises reacting a biguanide derivative of the formula,

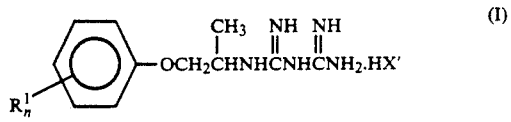

wherein $R^1$ and n are as defined in the formula (III), and X' is a halogen atom,
with a halocarboxylic acid ester of the formula,

wherein $R^2$ and X are as defined in the formula (III), and $R^3$ is a $C_1$-$C_4$ alkyl group,
in the presence of a base wherein a dehydrating agent is present in the reaction system.

The gist of the second aspect of the present invention consists in a process for producing 2-fluoroisobutyric acid ester of the formula,

wherein $R^4$ is one member selected from the class consisting of an alkyl group, an aryl group, an aralkyl group and an alkoxyalkyl group,
which comprises reacting a methacrylic acid ester of the formula,

wherein $R^4$ is as defined above,
with a hydrogen fluoride source.

The gist of the third aspect of the present invention consists in a process for producing 2-fluoroisobutyric acid ester of the formula (VII),

wherein $R^5$ is a lower alkyl group, a lower alkoxy lower alkyl group or a benzyl group,
which comprises reacting 2-haloisobutyric acid ester of the formula (VI),

wherein X" is a halogen atom other than fluorine, and $R^5$ is as defined above,
with a metal fluoride in the presence of a solvent.

DETAILED DESCRIPTION OF THE INVENTION

In the process for producing a triazine derivative as a first aspect of the present invention, the biguanide derivative of the above formula (I) and the halocarboxylic acid ester of the above formula (II) are used as starting materials.

In the formula (I) for the biguanide derivative as one of the starting materials, $R^1$ substituted on the terminal phenyl group is a $C_1$-$C_4$ alkyl group such as methyl, ethyl, linear or branched propyl, or linear or branched butyl. The subindex, n, showing the number of $R^1$'s is an integer of 0 to 2. When n is 0, it means that no $R^1$ is substituted on the terminal phenyl group. When n is 1, it means that one $R^1$ is substituted on the terminal phenyl group. When n is 2, it means that two $R^1$'s, which may be the same or different, are substituted on the terminal phenyl group. $X'$ in the formula (I) is a halogen such as chlorine, bromine, iodine or fluorine.

In the formula (II) for the halocarboxylic acid ester as the other starting material, $R^2$ is hydrogen or a $C_1$-$C_2$ alkyl group such as methyl or ethyl, $R^3$ is a $C_1$-$C_4$ alkyl group such as methyl, ethyl, linear or branched propyl, or a linear or branched butyl, and X is a halogen atom such as chlorine, bromine, iodine or fluorine.

In the present invention, the formula (II) compound/formula (I) compound molar ratio is preferably 0.5 to 5.0. When this molar ratio is less than 0.5, the yield of the intended triazine derivative is low. On the other hand, even when it exceeds 5.0, no further improvement in the yield can be expected. This molar ratio is particularly preferably 1.0 to 3.0.

According to the present invention, the compound of the formula (I) and the compound of the formula (II) are allowed to react in the presence of a base. The base is selected from (1) metal alkoxides such as sodium methoxide and sodium ethoxide, (2) salts of week acids and strong bases such as sodium phosphate and sodium carbonate, and (3) organic bases such as DBU (1,8-diazabicyclo[5,4,0]undec-7-ene) and DBN (1,5-diazabicyclo[4,3,0]non-5-ene). This base not only works as a catalyst to promote the reaction between the compound of the formula (I) and the compound of the formula (II) but also takes a role to neutralize free hydrohalogenic acid generated during the reaction. The amount of the base is preferably 1.0 to 5.0 mol per mole of the compound of the formula (I). When this amount is less than 1.0 mol, the yield of the intended product is low. On the other hand, even when it exceeds 5.0 mol, no further improvement in the yield can be expected. The amount of the base is particularly preferably 1.0 to 3.0 mol per mole of the compound of the formula (I).

The process for producing a triazine derivative, provided by the present invention, is characterized by the presence of a dehydrating agent in the reaction system when the compound of the above formula (I) and the compound of the above formula (II) are allowed to react in the presence of the base to produce the triazine derivative of the formula (III),

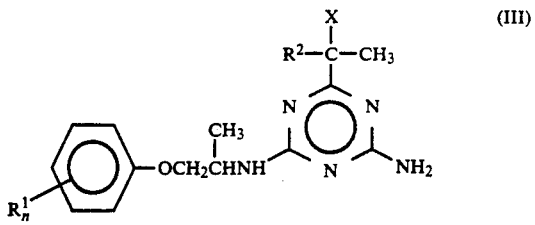

wherein $R^1$, n, $R^2$ and X are as already defined.

The dehydrating agent prevents the hydrolysis of the halocarboxylic acid ester of the formula (II) caused by water formed during the reaction as a byproduct. Therefore, the intended substance, the triazine derivative, can be obtained at a higher yield in the process of the present invention than in the aforementioned conventional processes. The dehydrating agent is selected from (1) natural or synthetic zeolite, and (2) anhydrous sulfates such as anhydrous sodium sulfate, anhydrous magnesium sulfate and anhydrous calcium sulfates. The (1) natural or synthetic zeolite may be in any one of the forms of a column, a sphere, granules and apowder. In view of dehydration capability, it is preferred to use synthetic zeolite of A-type, particularly of 3A-type. The amount of the dehydrating agent for use is preferably 0.1 to 10 times the weight of the compound of the formula (I). When this amount is less than 0.1 times, the dehydration effect is low. On the other hand, even when it exceeds 10 times, no further improvement can be expected in the yield of the intended product. The amount of the dehydrating agent for use is particularly preferably 0.4 to 2.0 times.

The above reaction is generally carried out in a solvent. The solvent is selected from (1) alcohols such as methanol, ethanol, isopropanol and n-octanol, (2) ethers such as tetrahydrofuran, 1,4-dioxane, methyl cellosolve and tert-butyl methyl ether, (3) ketones such as acetone and methyl ethyl ketone, (4) aprotic polar solvents such as dimethylformamide (hereinafter referred to as DMF), dimethylsulfoxide (hereinafter referred to as DMSO) and acetonitrile, (5) aromatic hydrocarbons such as toluene and xylene, and (6) halogenated hydrocarbons such as chloroform and dichlormethane. In view of solubility, preferred are alcohols such as methanol, ethanol and octanol, methyl cellosolve and DMF. The amount of the solvent for use is preferably 1 to 30 times the weight of the compound of the formula (I). When this amount is smaller than the amount of the compound of the formula (I), the starting materials can be hardly dissolved. On the other hand, when it exceeds 30 times, the solvent amount is too large to be economical. The amount of the solvent is particularly preferably 3 to 10 times.

The reaction temperature and the reaction time are not critial. In order to carry out the reaction smoothly and improve the yield, the reaction temperature is $-30°$ to 150° C., preferably $-10°$ to 65° C., and the reaction time is preferably in the ragne of 30 minutes to 20 hours although it depends on the reaction temperature. The reaction pressure may be atmospheric pressure or elevated pressure.

In the above-described process for producing a triazine derivative, provided by the present invention, the compound of the formula (I) and the compound of the formula (II) are allowed to react in the presence of both the base and the dehydrating agent. Therefore, the hydrolysis of the compound of the formula (II) by water formed as a byproduct during the reaction can be prevented, and the triazine derivative of the formula (III) can be obtained at high yields.

The second aspect of the present invention will be detailed hereinafter.

In the process for producing 2-fluroisobutyric acid ester, provided by the present invention, the methacrylic acid ester used as a starting material includes methacrylic acid esters of the formula (IV),

   (IV)

wherein $R^4$ is one selected from the class consisting of an alkyl group, an aryl group, an aralkyl group and an alkoxyalkyl group.

In the formula (IV) for the methacrylic acid ester, the alkyl group as $R^4$ includes $C_1-C_{18}$ alkyl and $C_5$ and $C_6$ cycloalkyl groups such as methyl, ethyl, n-propyl, isopropyl, n-butyl, isobutyl, tert-butyl, 2-ethylhexyl, tridecyl, stearyl, cyclohexyl and cyclopentyl. The aryl group as $R^4$ includes a $C_6-C_7$ aryl group such as phenyl, 2-methylphenyl, 4-methylphenyl, 4-chlorophenyl and 4-nitrophenyl. The aralkyl group as $R^4$ includes a $C_7-C_8$ aralkyl group such as benzyl, 2-methylbenzyl, 4-methylbenzyl, 4-chlorobenzyl and 4-nitrobenzyl. The alkoxyalkyl group as $R^4$ includes $C_1-C_4$ alkoxy $C_2-C_4$ alkyl group such as methoxyethyl, ethoxyethyl, propoxyethyl, butoxyethyl, ethoxybutyl and methoxybutyl.

In the process for producing 2-fluoroisobutyric acid ester, provided by the present invention, the hydrogen fluoride source which is allowed to react with the above methacrylic acid ester is selected from anhydrous hydrogen fluoride and amine-containing hydrogen fluoride (the hydrogen fluoride/amine weight ratio is generally 50/50 to 99/1, preferably 70/30 to 95/5). The above amine includes aromatic amines such as pyridine, melamine and collidine, and tertiary aliphatic amines such as trimethylamine, triethylamine and tributylamine. The above hydrogen fluoride source is preferably in an anhydrous state. The "anhydrous state" means a substantially anhydrous state, and a small amount of water may be present (for example, about 1% by weight or less based on anhydrous hydrogen fluoride or amine-containing hydrogen fluoride). The above hydrogen fluoride source is required to be in a hydrogen fluoride state only during the reaction with the methacrylic acid ester. Therefore, a hydrogen fluoride precursor may be charged in the reaction system to generate hydrogen fluoride in the reaction system.

In the process of the present invention, 2-fluoroisobutyric acid ester can be obtained with high selectivity even if the hydrogen fluoride source is allowed to react with methacrylic acid ester in the absence of a catalyst, while the use of a Lewis acid catalyst further improves the yield. The Lewis acid catalyst includes sulfuric acid ($H_2SO_4$), methanesulfonic acid ($CH_3SO_3H$), trifluoromethanesulfonic acid ($CF_3SO_3H$), fluorosulfuric acid ($FSO_3H$), aluminum chloride ($AlCl_3$), aluminum fluoride ($AlF_3$), zinc chloride ($ZnCl_2$), ferric chloride ($FeCl_3$), tin chloride ($SnCl_4$), titanium chloride ($TiCl_4$) and antimony pentafluoride ($SbF_5$).

Although not being critical, the reaction temperature is preferably 20° to 150° C., particularly preferably 50° to 120° C. The reaction pressure is not critical, either. Any one of atmospheric pressure and elevated pressures may be employed.

The third aspect of the present invention will be detailed hereinafter.

In the process for producing 2-fluoroisobutyric acid ester, provided by the present invention, the haloisobutyric acid ester used as a starting material has the following formula (VI),

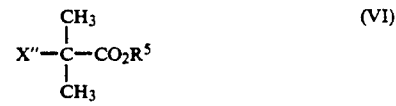   (VI)

wherein X" is a halogen atom other than fluorine, and $R^5$ is a lower alkyl group, a lower alkoxy lower alkyl group or a benzyl group.

In the formula (VI), the halogen atom represented by X" includes I, Br and Cl, and Br is preferred. The lower alkyl group represented by $R^5$ includes a $C_1-C_6$ alkyl group such as methyl, ethyl and propyl. The lower alkoxy lower alkyl group represented by $R^5$ includes $C_1-C_6$ alkoxy $C_1-C_6$ alkyl group such as methoxyethyl, ethoxy ethyl and propoxyethyl.

The metal fluoride used in the present invention includes metal fluorides such as cuprous fluoride, potassium fluoride and cesium fluoride. Preferred are alkali metal fluorides such as potassium fluoride and cesium fluoride. The above metal fluorides may be used alone or in combination. The amount of the metal fluoride for use per mole of the compound of the formula (VI) is 0.7 to 4.0 mol, preferably 1.1 to 2.0 mol.

The solvent used in the present invention includes aprotic polar solvents such as acetonitrile, DMF and DMSO; $C_1-C_5$ alcohols such as methanol, ethanol, propanol, butanol, ethoxyethanol, ethylene glycol, 2,3-butanediol and 1,2-propanediol; and ether polar solvents such as diethylene glycol diethyl ether. Preferred are $C_1-C_5$ alcohols. The amount of the solvent for use per mole of the compound of the formula (VI) is 0.5 to 10.0 mol, preferably 1.0 to 2.5 mol.

The reaction temperature is generally 50° to 180° C., preferably 80° to 140° C. The reaction time is generally 5 to 60 hours, preferably 5 to 40 hours.

According to the above process of the present invention, 2-fluoroisobutyric acid ester can be produced from haloisobutyric acid ester safely, at a low cost and at high yields.

According to the above process of the present invention, 2-fluoroisobutyric acid ester can be obtained at a single step with high selectivity at a low cost. Therefore, the above process of the present invention is industrially highly significant.

The present invention will be further detailed by reference to Examples, to which, however, the present invention shall not be limited.

First, Examples on the production of triazine derivatives will be described.

EXAMPLE 1

4.71 Grams (15.7 mmol) of 2-(3',5'-dimethylphenoxy)isopropylbiguanide hydrochloride of the formula,

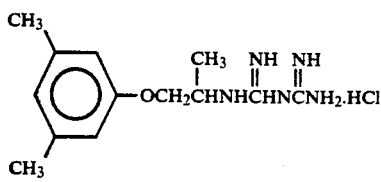

was dissolved in 30 ml of dry methanol, and 4.5 g of synthetic zeolite (3A type, column form) as a dehydrating agent was added. The amount of the used zeolite was 0.96 times the weight of the biguanide derivative. While the mixture was stirred at room temperature, sodium methoxide prepared from 0.77 g (33.5 mmol) of sodium and 20 ml of dry methanol was added, and then, 2.20 g (18.4 mmol) of methyl α-fluoro-α-methylpropionate of the following formula.

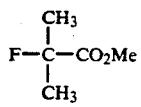

was added dropwise. Then, the mixture was stirred at 20° C. for 2 hours and at 65° C. for 2 hours. After the synthetic zeolite was separated by filtration, the filtrate was concentrated under reduced pressure, and then 50 ml of ethyl acetate and 50 ml of water were added for extraction. The organic layer was washed with water, dried over anhydrous sodium sulfate, and concentrated under reduced pressure to give 4.64 g of an oily substance. This substance was analyzed by high pressure liquid chromatography (hereinafter referred to as HPLC) to show that the purity of the intended substance was 89% and that the yield thereof was as high as 79%. It was found that this substance was 2-amino-4-[2-(3′,5′-dimethylphenoxy)-isopropylamino]-6-(α-fluoroisopropyl)-s-triazine of the following formula.

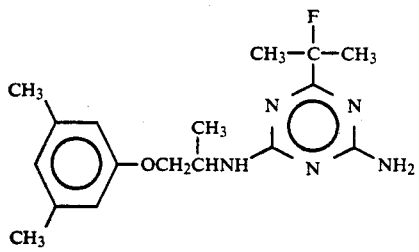

EXAMPLES 2–14

Example 1 was repeated except for the use of biguanide derivatives and halocarboxylic acid esters in amounts shown in Table 1, bases and dehydrating agents shown in Table 1 in amounts shown in Table 1 and reaction conditions shown in Table 1 to give the same intended products as that obtained in Example 1. As shown in Table 1, the yields in Examples 2 to 14 were as high as 71 to 92%. In particular, when synthetic zeolite of 3A type was used as a dehydrating agent, excellent results were obtained in terms of the yields.

COMPARATIVE EXAMPLE 1

Example 1 was repeated except that no hydrating agent was used. As shown in Table 1, the yield was as low as 61%.

EXAMPLE 15

5.00 Grams (16.7 mmol) of 2-(3′,5′-dimethylphenoxy)isopropylbiguanide hydrochloride was dissolved in 15 ml of dry methanol, and 4.5 g of synthetic zeolite (3A type, powder form) was added. While the mixture was stirred at −10° C., 1.80 g (33.4 mmol) of sodium methoxide (supplied by Kanto Chemical Co., Ltd.), and then 2.20 g (18.4 mmol) of methyl α-fluoro-α-methylpropionate was added dropwise. The mixture was further stirred at −10° C. for 12 hours. After the synthesis zeolite was separated by filtration, the filtrate was concentrated under reduced pressure, and then 50 ml of ethyl acetate and 50 ml of water were added for extraction. The organic layer was washed with water, dried over anhydrous sodium sulfate and concentrated under reduced pressure to give 5.25 g of an oily substance. This substance was analyzed by HPLC to show that the purity of the intended product. 2-amino-4-[2-(3′,5′-dimethylphenoxy)isopropylamino]-6-(α-fluoroisopropyl)-s-triazine, was 97% and the yield thereof was 92%.

EXAMPLES 16–25

Example 15 was repeated except for the use of bases, dehydrating agents and solvents shown in Table 1 in amounts shown in Table 1 and reaction conditions shown in Table 1.

As shown in Table 1, the yields in Examples 15 to 25 were as high as 81 to 95% and higher than the yields in Examples 1 to 14. In particular, when alcohols were used as a solvent and synthetic zeolite was used as a dehydrating agent, excellent results were obtained in terms of the yields.

TABLE 1

| Example No. | Biguanide derivative* | Halocarboxylic acid ester** | Base | | Dehydrating agent | | Solvent | Temperature•Time | Yield |
| --- | --- | --- | --- | --- | --- | --- | --- | --- | --- |
| 1 | 4.71 g (15.7 mmol) | 2.20 g (18.4 mmol) | sodium methoxide | 1.81 g (33.5 mmol) | synthetic zeolite (3A type, column) | 4.5 g | methanol | (20° C., 2 hours) + (65° C., 2 hours) | 79% |
| 2 | 5.00 g (16.7 mmol) | 2.20 g (18.4 mmol) | sodium methoxide | 1.81 g (33.5 mmol) | synthetic zeolite (3A type, column) | 9.0 g | methanol | (20° C., 2 hours) + (65° C., 2 hours) | 80% |
| 3 | 5.00 g (16.7 mmol) | 3.00 g (25.0 mmol) | sodium methoxide | 1.81 g (33.5 mmol) | synthetic zeolite (3A type, column) | 9.0 g | methanol | (20° C., 2 hours) + (65° C., 2 hours) | 92% |
| 4 | 5.00 g (16.7 mmol) | 2.20 g (18.4 mmol) | sodium methoxide | 2.70 g (50.0 mmol) | synthetic zeolite (3A type, column) | 9.0 g | methanol | (20° C., 2 hours) + (65° C., 2 hours) | 76% |

TABLE 1-continued

| Example No. | Biguanide derivative* | Halocarboxylic acid ester** | Base | | Dehydrating agent | | Solvent | Temperature•Time | Yield |
|---|---|---|---|---|---|---|---|---|---|
| 5 | 5.00 g (16.7 mmol) | 2.20 g (18.4 mmol) | sodium methoxide | 1.08 g (20.0 mmol) | synthetic zeolite (3A type, column) | 4.5 g | methanol | (20° C., 19 hours) | 77% |
| 6 | 5.00 g (16.7 mmol) | 2.20 g (18.4 mmol) | sodium methoxide | 1.08 g (20.0 mmol) | synthetic zeolite (3A type, column) | 4.5 g | methanol | (65° C., 5 hours) | 72% |
| 7 | 5.00 g (16.7 mmol) | 2.20 g (18.4 mmol) | sodium methoxide | 1.35 g (25.1 mmol) | synthetic zeolite (3A type, column) | 4.5 g | methanol | (20° C., 7 hours) | 76% |
| 8 | 5.00 g (16.7 mmol) | 2.20 g (18.4 mmol) | sodium methoxide | 1.35 g (25.1 mmol) | synthetic zeolite (3A type, powdery) | 4.5 g | methanol | (20° C., 4.5 hours) | 83% |
| 9 | 5.00 g (16.7 mmol) | 2.20 g (18.4 mmol) | sodium phosphate | 5.47 g (33.4 mmol) | synthetic zeolite (3A type, column) | 4.5 g | methanol | (20° C., 11.5 hours) | 70% |
| 10 | 5.00 g (16.7 mmol) | 2.20 g (18.4 mmol) | sodium methoxide | 1.81 g (33.5 mmol) | anhydrous calcium sulfate | 4.5 g | methanol | (20° C., 15 hours) | 73% |
| 11 | 4.71 g (15.7 mmol) | 2.20 g (18.4 mmol) | sodium methoxide | 1.81 g (33.5 mmol) | anhydrous sodium sulfate | 2.4 g | methanol | (20° C., 15 hours) | 73% |
| 12 | 4.71 g (15.7 mmol) | 2.20 g (18.4 mmol) | sodium methoxide | 1.81 g (33.5 mmol) | anhydrous magnesium sulfate | 2.0 g | methanol | (20° C., 15 hours) | 71% |
| 13 | 5.00 g (16.7 mmol) | 2.60 g (21.7 mol) | sodium methoxide | 1.35 g (25.1 mmol) | synthetic zeolite (3A type, powdery) | 4.5 g | methanol | (20° C., 5.5 hours) | 90% |
| 14 | 5.00 g (16.7 mmol) | 2.20 (18.4 mmol) | sodium methoxide | 1.35 g (25.1 mmol) | synthetic zeolite (3A type, powdery) | 9.0 g | methanol | (20° C., 7 hours) | 86% |
| Comparative Example 1 | 15.0 g (50.0 mmol) | 6.60 g (55.0 mmol) | sodium methoxide | 4.05 g (75.0 mmol) | — | — | methanol | (65° C., 4 hours) | 61% |
| 15 | 5.00 g (16.7 mmol) | 2.20 g (18.4 mmol) | sodium methoxide | 1.80 g (33.4 mmol) | synthetic zeolite (3A type, powdery) | 4.5 g | methanol | (−10° C., 12 hours) | 92% |
| 16 | 5.00 g (16.7 mmol) | 2.20 g (18.4 mmol) | sodium methoxide | 1.35 g (25.1 mmol) | synthetic zeolite (3A type, powdery) | 4.5 g | ethanol | (0° C., 23 hours) | 93% |
| 17 | 5.00 g (16.7 mmol) | 2.20 g (18.4 mmol) | sodium methoxide | 1.35 g (25.1 mmol) | synthetic zeolite (3A type, powdery) | 4.5 g | n-octanol | (0° C., 24 hours) | 95% |
| 18 | 5.00 g (16.7 mmol) | 2.20 g (18.4 mmol) | sodium methoxide | 1.35 g (25.1 mmol) | synthetic zeolite (3A type, powdery) | 4.5 g | tert-butyl methyl ether | (0° C., 23 hours) | 81% |
| 19 | 5.00 g (16.7 mmol) | 2.20 g (18.4 mmol) | sodium methoxide | 1.35 g (25.1 mmol) | synthetic zeolite (3A type, powdery) | 4.5 g | methyl cellosolve | (0° C., 21 hours) | 94% |
| 20 | 5.00 g (16.7 mmol) | 2.20 g (18.4 mmol) | sodium methoxide | 1.35 g (25.1 mmol) | synthetic zeolite (3A type, powdery) | 4.5 g | DMF | (−10° C., 3 hours) | 88% |
| 21 | 5.00 g (16.7 mmol) | 2.20 g (18.4 mmol) | sodium methoxide | 1.35 g (25.1 mmol) | synthetic zeolite (3A type, powdery) | 4.5 g | dichloromethane | (0° C., 4 hours) | 84% |
| 22 | 5.00 g (16.7 mmol) | 2.20 g (18.4 mmol) | sodium methoxide | 1.35 g (25.1 mmol) | anhydrous calcium sulfate | 4.5 g | methanol | (0° C., 24 hours) | 89% |
| 23 | 5.00 g (16.7 mmol) | 2.20 g (18.4 mmol) | sodium methoxide | 1.35 g (25.1 mmol) | anhydrous calcium sulfate | 4.5 g | DMF | (0° C., 21 hours) | 82% |
| 24 | 5.00 g (16.7 mmol) | 2.20 g (18.4 mmol) | sodium methoxide | 1.35 g (25.1 mmol) | anhydrous calcium sulfate | 4.5 g | toluene | (0° C., 24 hours) | 83% |
| 25 | 5.00 g (16.7 mmol) | 2.20 g (18.4 mmol) | DBU*** | 3.81 g (25.0 mmol) | synthetic zeolite (3A type, | 4.5 g | methanol | (65° C., 15 hours) | 82% |

TABLE 1-continued

| Example No. | Biguanide derivative* | Halocarboxylic acid ester** | Base | Dehydrating agent | Solvent | Temperature•Time | Yield |
|---|---|---|---|---|---|---|---|
| | | | | powdery) | | | |

*Biguanide derivative: 2-(3',5'-dimethylphenoxy)isopropylbiguanide hydrochloride
**Halocarboxylic acid ester: methyl α-fluoro-α-methylpropionate
***DBU: 1,8-diazabicyclo[5,4,0]undec-7-ene Examples on the production of 2-fluoroisobutyric acid ester as an intermediate compound for the production of a triazine derivative according to the process of the second aspect of the present invention will be described hereinafter.

EXAMPLE 26

A 150 ml autoclave having an internal cylinder made of polytetrafluoroethylene (called Teflon) was charged with 10 g (0.1 mol) of methyl methacrylate, 70 ml of a hydrogen fluoride/pyridine mixture (having a hydrogen fluoride/pyridine weight ratio of 70/30 and containing about 3 mol of hydrogen fluoride) and 35 g (0.35 mol) of fluorosulfuric acid, and the resultant mixture was heated at 100° C. for 7 hours. Then, the reaction mixture was cooled, poured into ice water, and subjected to extraction with 50 ml of methylene chloride three times. The extract was washed with saturated sodium hydrogencarbonate and with a saturated aqueous sodium chloride solution, and then dried over anhydrous sodium sulfate. The organic layer was filtered, and a solid on a paper filter was washed with methylene chloride several times. The filtrate and the wash liquid were mixed, and after methylene chloride was distilled off under reduced pressure, the remainder was distilled to give methyl 2-fluoroisobutyrate (boiling point: 70° C. (150 mmHg)).

The yield of the methyl 2-fluoroisobutyrate was 1.8 g, or 15%, and the selectivity was 100%.

EXAMPLES 27–38

Example 26 was repeated except that the reaction conditions shown in Table 2 were applied to give results shown in Table 2.

reaction is carried out in the absence of a Lewis acid catalyst, the yield of methyl 2-fluoroisobutyrate can be improved by setting a longer reaction time. This point is clear in comparison of the result (yield: 6%) of Example 27 in which the reaction was carried out in the absence of a Lewis acid catalyst at 120° C. for 7 hours and the result (yield 12%) of Example 28 in which the reaction was carried out in the absence of a Lewis acid catalyst at 120° C. for 28 hours.

(ii) As is clear in Examples 26 and Examples 29 to 34, the use of any one of various Lewis acid catalysts gives methyl 2-fluorisobutyrate with selectivity of 100%.

Next, examples on the production of 2-fluoroisobutyric acid ester according to the process of the third aspect of the present invention will be described hereinafter.

EXAMPLE 39

7.15 Grams (0.123 mol) of preliminarily dehydrated and dried KF and 20 g (0.103 mol) of ethyl 2-bromoisobutyrate were added to 40 g of 2,3-butanediol purified by distillation. While the resultant mixture was stirred in an oil bath at a reaction temperature of 120° to 125° C., it was allowed to react for 16 hours. After the reaction, the reaction mixture was poured into water, and subjected to extraction with diethyl ether three times. The ether solution of the so-obtained product was quantitatively determined by using p-xylene as an internal standard compound to show that the yield of ethyl 2-fluoroisobutyrate was 45%, which value was higher than that achieved by a conventional process.

EXAMPLES 40–43

Example 39 was repeated except that the reaction

TABLE 2

| | Reaction Conditions | | | | Reaction Results | |
|---|---|---|---|---|---|---|
| Example | HF source | Catalyst | Temperature (°C.) | Time (hr) | Yield (%) | Selectivity (%) |
| 26 | 70% HF/30% Py 70 ml | FSO₃H (0.35M) | 100 | 7 | 15 | 100 |
| 27 | " | — | 120 | 7 | 6 | " |
| 28 | " | — | " | 28 | 12 | " |
| 29 | " | CH₃SO₃H (0.4M) | " | 7 | 9 | " |
| 30 | " | CH₃SO₃H (0.35M) | 100 | " | 11 | " |
| 31 | " | CF₃SO₃H (0.35M) | " | " | 16 | " |
| 32 | " | H₂SO₄ (0.35M) | " | " | 7 | " |
| 33 | " | FSO₃H (0.35M) | 80 | " | 23 | " |
| 34 | " | " | 50 | 75 | 22 | " |
| 35 | 90% HF/10% Py 70 ml | — | 120 | 16.5 | 25 | " |
| 36 | 95% HF/5% Py 70 ml | — | " | " | 23 | " |
| 37 | anhydrous HF 70 ml | — | " | " | 16 | " |
| 38 | 95% HF/5% Py 70 ml water 0.7 ml | — | " | " | 25 | " |

"HF" stands for hydrogen fluoride, and "Py" stands for pyridine.
"%" stands for "%" by weight.

The above-described Examples show the following.

(i) Even when the reaction is carried out in the absence of a Lewis acid catalyst, methyl 2-fluoroisobutyrate can be obtained with selectivity of 100% (Examples 27 and 28, and Examples 35 to 38). Even when the conditions shown in Table 3 were applied. Table 3 shows the results. Table 3 clearly shows that ethyl 2-fluoroisobutyrate can be obtained at higher yields than a conventional process.

TABLE 3

| Example No. | Solvent | Metal fluoride | R | Reaction temperature (°C.) | Reaction time (hr) | Yield (%) |
|---|---|---|---|---|---|---|
| 39 | 2,3-butanediol 40 g | KF 0.123 mol | ethyl | 120–125 | 16 | 45 |
| 40 | ethoxyethanol 40 g | KF 0.155 mol | " | 130 | 17 | 43 |
| 41 | ethylene glycol 40 g | KF 0.113 mol | " | 125 | 10 | 44 |
| 42 | 2,3-butanediol 20 g | CsF 0.123 mol | " | 120 | 6 | 52 |
| 43 | acetonitrile 40 g | KF 0.123 mol | benzyl | 83 | 40 | 28 |

As specified above, the present invention has enabled the production of triazine derivatives at high yields by allowing a dehydrating agent to be co-present when a biguanide derivative and a halocarboxylic acid ester are allowed to react in the presence of a base.

Further, the present invention has provided a process for producing 2-fluoroisobutyric acid ester, an intermediate compound for the production of the above biguanide derivative, from methacrylic acid ester at a single step with high selectivity at a low cost.

Furthermore, the present invention has provided a process for producing 2-fluoroisobutyric acid ester from haloisobutyric acid ester at high yields, safely and at a low cost.

What is claimed is:

1. A process for producing a triazine derivative of the formula (III).

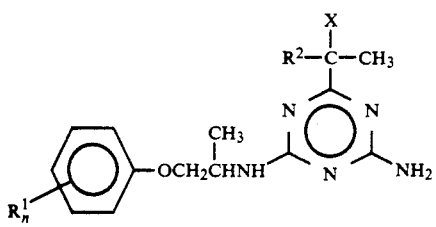

(III)

wherein $R^1$ is a $C_1$–$C_4$ alkyl group, n is an integer of 0 to 2, $R^2$ is hydrogen or a $C_1$–$C_2$ alkyl group, and X is a halogen atom,
which comprises reacting a biguanide derivative of the formula,

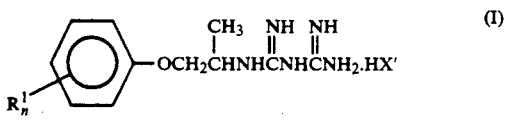

(I)

wherein $R^1$ and n are as defined in the formula (III), and X' is a halogen atom,
with a halocarboxylic acid ester of the formula,

(II)

wherein $R^2$ and X are as defined in the formula (III), and $R^3$ is a $C_1$–$C_4$ alkyl group,
in the presence of a base, wherein a dehydrating agent is present in the reaction system.

2. The process according to claim 1, wherein the dehydrating agent is synthetic zeolite or anhydrous sulfate.

3. The process according to claim 1, wherein the dehydrating agent is used in an amount 0.1 to 10 times as large as the amount of the compound of the formula (I).

4. The process according to claim 1, wherein the dehydrating agent is used in an amount 0.4 to 2.0 times as large as the amount of the compound of the formula (I).

5. The process according to claim 1, wherein a molar ratio of the compound of the formula (II) to the compound of the formula (I) is 0.5 to 5.0.

6. The process according to claim 1, wherein a molar ratio of the compound of the formula (II) to the compound of the formula (I) is 0.5 to 3.0.

7. The process according to claim 1, wherein the base is at least one member selected from the group consisting of metal alkoxides, salts of weak acids and strong bases, and organic bases.

8. The process according to claim 1, wherein the base is used in an amount of 1.0 to 5.0 mol per mole of the compound of the formula (I).

9. The process according to claim 1, wherein the base is used in an amount of 1.0 to 3.0 mol per mole of the compound of the formula (I).

10. The process according to claim 1, wherein one or more members selected from the group consisting of alcohols, ethers, ketones, aprotic polar solvents, aromatic hydrocarbons and halogenated hydrocarbons are used as a solvent.

11. The process according to claim 10, wherein the solvent is at least one member selected from the group consisting of methanol, ethanol, n-octanol, methyl cellosolve and DMF.

12. The process according to claim 10, wherein the solvent is used in an amount 1 to 30 times as large as the weight of the compound of the formula (I).

13. The process according to claim 10, wherein the solvent is used in an amount 3 to 10 times as large as the weight of the compound of the formula (I).

14. The process according to claim 1, wherein the halocarboxylic acid ester is a 2-fluoroisobutyric acid ester of the formula,

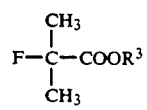

wherein $R^3$ is as defined in the claim 1.

15. The process according to claim 1, wherein the base is selected from the group consisting of sodium methoxide; sodium ethoxide; sodium phosphate; sodium carbonate; 1,8-diazabicyclo (5,4,0)undec-7-ene; and 1,5-diazabicyclo(4,3,0)non-5-ene.

16. The process according to claim 15, wherein the dehydrating agent is selected from the group consisting of a natural zeolite, a synthetic zeolite, anhydrous sodium sulfate, anhydrous magnesium sulfate and anhydrous calcium sulfate.

17. The process according to claim 15, wherein the dehydrating agent is 3A-type synthetic zeolite.

18. The process according to claim 16, wherein the solvent is selected from the group consisting of methanol, ethanol, isopropanol, n-octanol, tetrahydrofuran, 1,4-dioxane, methyl cellosolve, tert-butyl methyl ether, acetone, methyl ethyl ketone, dimethylformamide, dimethylsulfoxide, acetonitrile, toluene, xylene, chloroform and dichloromethane.

19. The process according to claim 18, wherein the process is carried out at a temperature of $-30°$ to $+150°$ C. for 30 minutes to 20 hours.

20. The process according to claim 2, wherein the dehydrating agent is in an amount of 0.4 to 2.0 times the amount of the compound of formula (I); the molar ratio of the compound of the formula (II) to the compound of formula (II) is 1.0 to 3.0; the base is selected from the group consisting of sodium methoxide; sodium ethoxide; sodium phosphate; sodium carbonate; 1,8-diazabicyclo (5,4,0)undec-7-ene; and 1,5-diazabicyclo(4,3,0)non-5-ene; the base is in an amount of 1.0 to 3.0 mole per mole of the compound of formula (I); the solvent is selected from the group consisting of methanol, ethanol, n-octanol, methyl cellosolve and dimethylformamide; the solvent is in an amount of 3 to 10 times the weight of the compound of formula (I); and the process is carried out at a temperature of $-30°$ to $+150°$ C.

* * * * *